(12) United States Patent
Woodaman

(10) Patent No.: US 6,270,724 B1
(45) Date of Patent: Aug. 7, 2001

(54) DETECTION OF CONTAMINANTS IN FOOD

(75) Inventor: James G. Woodaman, Pasadena, CA (US)

(73) Assignee: California South Pacific Investors, Pasadena, CA (US)

( * ) Notice: Subject to any disclaimer, the term of this patent is extended or adjusted under 35 U.S.C. 154(b) by 0 days.

(21) Appl. No.: 09/287,950

(22) Filed: Apr. 7, 1999

Related U.S. Application Data

(63) Continuation-in-part of application No. 09/246,064, filed on Feb. 8, 1999, now abandoned, which is a continuation of application No. 09/052,361, filed on Mar. 31, 1998, now Pat. No. 5,869,341, which is a continuation of application No. 08/758,205, filed on Nov. 26, 1996, now abandoned, which is a continuation-in-part of application No. 08/584,984, filed on Jan. 11, 1996, now abandoned.

(60) Provisional application No. 60/027,412, filed on Sep. 30, 1996.

(51) Int. Cl.$^7$ .................................................... G01N 33/12
(52) U.S. Cl. .................. 422/58; 436/1; 426/87; 426/232; 116/106
(58) Field of Search ............... 436/1, 164; 422/56, 422/58, 61; 426/87, 232; 116/100, 106

(56) References Cited

U.S. PATENT DOCUMENTS

| | | |
|---|---|---|
| 2,485,566 | 10/1949 | Clark . |
| 3,067,015 | 12/1962 | Lawdermilt . |
| 4,285,697 | 8/1981 | Neary . |
| 4,746,616 | 5/1988 | Honigs et al. . |
| 5,053,339 | 10/1991 | Patel . |
| 5,306,466 | 4/1994 | Goldsmith . |
| 5,869,341 | * 2/1999 | Woodaman ............... 436/1 |
| 6,190,610 | * 2/2001 | Goldsmith et al. ........ 436/1 |

FOREIGN PATENT DOCUMENTS

WO 94/27144   11/1994   (WO) .

* cited by examiner

Primary Examiner—Lyle A. Alexander
(74) Attorney, Agent, or Firm—Lyon & Lyon LLP

(57) ABSTRACT

The present invention relates to a food contamination detector associated with a double bar code, given the trademark GILBAR™ by the owner of the present invention, that includes coded indicia used to identify the presence of conditions indicative of microbial contamination in food, including toxic contaminants, bacterial metabolites, and other microbial secretions. Of the two bar code symbols associated with the food contamination detector, the first identifies the food product in terms of the type of food, the quantity, the price and the like, while the second bar code symbol is designed to identify the presence of contaminants. When contamination is not detected, the first bar code symbol is scanner readable, whereas the second bar code symbol is not. Once contamination is detected, bars in both bar code symbols can appear or disappear causing the first bar code symbol to become scanner unreadable and the second bar code symbol to become scanner readable.

6 Claims, 9 Drawing Sheets

DETECTION OF CONTAMINANTS IN FOOD

CROSS-REFERENCES TO RELATED APPLICATIONS

This is a continuation-in-part of U.S. application Ser. No. 09/246,064, filed Feb. 8, 1999, now abandoned, which is a continuation application of U.S. application Ser. No. 09/052,361, filed Mar. 31, 1998, now U.S. Pat. No. 5,869,341, issued Feb. 9, 1999, which is a continuation application of U.S. application Ser. No. 08/758,205, filed Nov. 26, 1996, now abandoned, which is a continuation-in-part of U.S. application Ser. No. 08/584,984, filed Jan. 11, 1996, now abandoned, which claims the benefit of U.S. Provisional Application Serial No. 60/027,412. Each of the above-mentioned applications are hereby incorporated by reference as if fully set forth herein.

FIELD OF THE INVENTION

The present invention relates to detection of the presence of conditions indicative of microbial contamination in food, including toxic contaminants, bacterial metabolites, and other microbial secretions.

BACKGROUND OF THE INVENTION

Over the past several years there has been increasing concern over the safety of our food supply. Contamination of food can come from a variety of sources and the type of contamination possible is often dependent on the food involved.

Most animal-derived food products, such as raw meat, are exposed to the possibility of contamination before, during, or after processing. Such contamination comes from, for example, contact with fecal matter at the slaughter house, from handlers of the food products at any stage of the processing of the food products, and from toxins, both naturally occurring and man-made, present in the environment where the food was grown or processed. In most cases, contamination is minor and, if the food is prepared properly, is not a serious threat to the consumer. However, while the contamination of food is generally low, i.e., few bacteria per gram of the food, if the food is not stored under satisfactory conditions or stored for long periods of time, contaminants, such as bacteria, grow to become a serious threat to the eventual consumer of the products. Even if the food products reach the market in an acceptable condition, subsequent treatment by the consumer may lead to the development of serious contamination of the food.

A common form of unsatisfactory storage condition involves inadequate temperature management throughout the cold chain. The cold chain is the course of distributing perishable foods from the supplier to the retailer to the consumer. In other words, the cold chain involves the refrigerated transport of food from the processor to the wholesaler, and all of the subsequent steps of storage, handling, and redistribution. Inadequate temperature management or temperature abuse of the food occurs when food is stored at temperatures above the optimal storage temperature and may occur at any point in the food distribution process.

Such time-temperature abuse of the food often results in considerable microbial growth and toxin production by microorganisms introduced through the diverse sources of contamination. Food-borne pathogens like bacteria flourish and increase to hazardous levels if the food is exposed to time-temperature abuse. The presence of bacteria in the food causes the production of off-odors and volatile gases, such as carbon dioxide, sulfur dioxide, hydrogen gas, and organic acids and nitrites in the food. Furthermore, certain kinds of bacteria, such as lactic acid bacteria, cause a decrease in the pH of the food, thus, enhancing further bacterial growth. Other bacteria produce various toxins often implicated in food-borne illnesses. The presence of off-odors, volatile gases, lowered pH, and toxins in the food are thus indicative of bacterial contamination of the food. These contamination-indicating conditions are often referred to as bacterial metabolites as they are the products and by-products of bacterial metabolism.

A number of incidents and factors have lead to the growing concern over food supply. These include:

- raw chicken and egg products have been found to be contaminated with Salmonella and inadequate cooking of such products has led to serious illness or death of persons who have consumed the contaminated products;
- inadequately pasteurized milk products have been found to be contaminated with Listeria that has lead to serious illness or death of consumers of the products;
- a highly toxic strain of *E. coli* has lead to the death of several people who consumed prepared beef products that had been inadequately cooked;
- a number of toxins are known, such as ciguatoxins, which contaminate fish. These toxins are not inactivated or destroyed by cooking and so their presence in fish is a threat to any consumer of the product;
- shell fish, such as oysters, concentrate any contaminants present in the water in which they grow and, since they are frequently eaten raw, pose a threat to the health of consumers; and
- fish is increasingly eaten raw which adds to the possibility of increased outbreak of illness from water-borne contaminants.

The only means the consumer has of determining if the food they purchase is contaminated is by visual inspection and by smell. These methods are usually inadequate to detect contamination.

There is a need for a reliable way to detect if a food product purchased by a consumer is fit for consumption. Any solution to this problem should be relatively inexpensive and able to detect a number of agents capable of causing illness. It should also be simple to "read" so that a consumer, who does not have access to sophisticated testing equipment or specialized knowledge, can readily determine if the products they have purchased are free from contamination.

SUMMARY OF THE INVENTION

The present invention relates to a detection system and most preferably to a food contamination detector associated with a double bar code, given the trademark GILBAR™ by the owner of the present invention, that includes coded indicia used to identify contaminated food. Of the two bar code symbols associated with the food contamination detector, the first identifies the food product in terms of the type of food, the quantity, the price and the like, while the second bar code symbol is designed to identify the presence of contaminants. When contamination is not detected, the first bar code symbol, the product bar code symbol, is scanner readable, whereas the second bar code symbol, the contamination code symbol, is not scanner readable. Once contamination is detected, bars in both bar code symbols can appear or disappear causing the first bar code symbol, the product bar code symbol, to become scanner unreadable and the second bar code symbol, the contamination bar code symbol, to become scanner readable.

The food contamination detector comprises an indicator linked to a means for detecting conditions indicative of contamination in food, including bacterial toxins and metabolites. Other contaminants may include microorganisms, such as viruses, toxins and other immunogenic materials or substances. The indicator used in each detector varies based upon the bacterial secretion, metabolite, or toxin being detected in the food. Typically, the means for detecting the contamination condition is either in communication with the juices from the food, or detects contaminants in the gases or vapors emanating from the food. Alternatively, ordinary flexible packaging film, such as commercial polyethylene produced under the registered mark SARANEX®, may be transformed into a composite material containing multiple sites per unit of surface area which can detect and identify multiple toxic microbial materials in a food package using the TOXIN GUARD™ system developed by Toxin Alert Incorporated and Skye Pharmatech Incorporated. The packaging film detector may be used in conjunction with the double bar code or GIL-BAR™ system.

A means for changing the appearance of the indicator when the bacterial metabolite, toxin, secretion, or other contamination condition, such as temperature abuse, is present in the vapors, gases or juices from the food, is provided to indicate that the food is contaminated. In one embodiment of the invention, the means for changing the appearance of the indicator comprises a labeled antibody that dissociates from the substrate in the presence of a bacterial metabolite, toxin, secretion, or other condition indicative of contamination. In another embodiment, the means for changing the appearance of the indicator comprises a labeled antibody that binds to the substrate in the presence of a bacterial metabolite, toxin, or other condition indicative of contamination. In another embodiment the change in appearance of the of the indicator results in a change in a bar code symbol or other coded indicia, words, or symbols. The change in the bar code symbol may either cause the bar code indicia to appear or disappear.

Other substances may be used in lieu of labeled antibodies as the means for changing the appearance of the indicator. For instance, a deoxyribonucleic acid (DNA) probe, or a ribonucleic acid (RNA) probe directed to nucleotide sequences of the microbial toxin, or to nucleotide sequences of the contaminating microorganism, itself, or further still, to nucleotide sequences of antigens secreted by the contaminating microorganism may be used.

In a further embodiment, a time-temperature indicator may be used to detect the presence of bacterial metabolites that have resulted from temperature abuse of the food product. The use of time-temperature indicators to detect temperature abuse of the food product in terms of bacterial growth is well known in the art. Typically, a time-temperature indicator employs enzymatic color indicators to show the amount of temperature exposure of the food product as evidenced by the pH change from a set basal limit. (See Blixt, et al., *An Enzymatic Time/Temperature Device for Monitoring the Handling of Perishable Commodities,* Dev. Biol. Stand., 36:237–41 (1976), which is hereby incorporated by reference as if fully set forth herein.)

In a yet further embodiment of the invention, the means for changing the appearance of the indicator may comprise a volatile gas sensor, capable of detecting the presence of volatile gases such as carbon dioxide, hydrogen gas, ammonia, organic acids, and nitrite intermediates in the vapors and gases from the food.

In one embodiment of the invention, the means for changing the appearance of the indicator and the substrate may be placed on the top of the food packaging, allowing gases and vapors to rise and come into contact with the means for changing the appearance of the indicator. In an alternate embodiment, the juices and liquids from the food may travel up via capillary action to come into contact with the means for changing the appearance of the indicator. In a yet further embodiment of the invention, the juices, gases, and vapors may collect in a particular area at the bottom of the detector, where they come into contact with the means for changing the appearance of the indicator and the substrate. The double bar code system or GILBAR™ may be used in conjunction with all the various embodiments described above.

BRIEF DESCRIPTION OF THE DRAWINGS

Other objects and features of the invention will become apparent from the following detailed description taken in connection with the accompanying drawings. It should be understood, however, that the drawings are intended for the purpose of illustration only, and are not to be taken as a definition of the limits of the invention.

In the drawings, wherein the same reference number denotes the same element throughout all of the views.

DETAILED DESCRIPTION OF THE PREFERRED EMBODIMENTS

Figure 1:
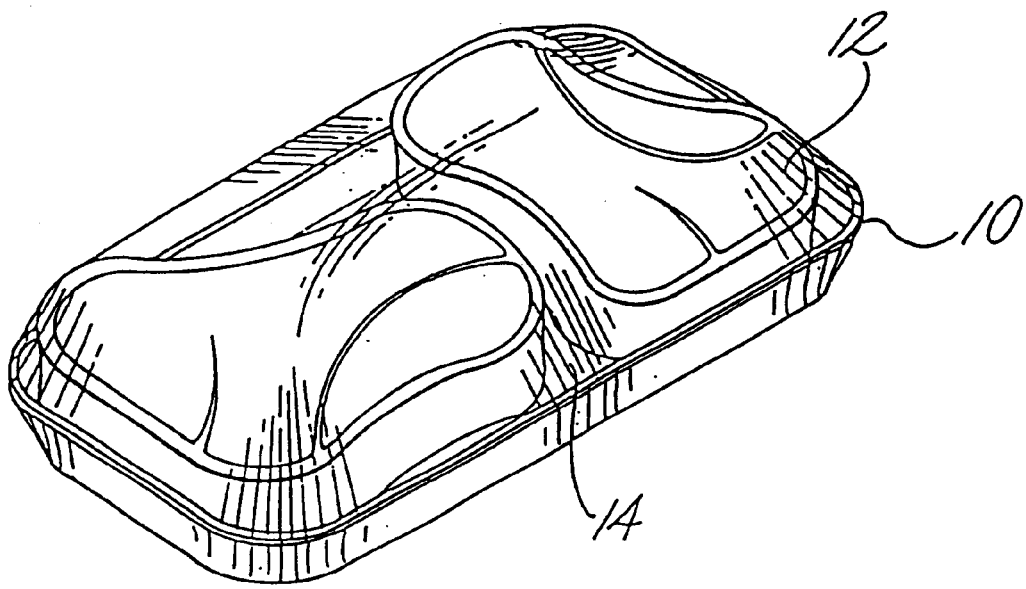
FIG. 1 is a top view of a packaged food product.

The present invention uses an indicator which may be in the form of words, symbols, a bar code, coded indicia, or part of a bar code or coded indicia that identifies a product at point of purchase, sale, or distribution as a detector system. The detector system disclosed herein is particularly adapted for use as a food detection system for detecting conditions indicative of contamination that may be present in food products, including bacterial metabolites, toxins, and other secretions. In alternative embodiments, ordinary flexible packaging film, such as commercial polyethylene produced under the registered mark SARANEX®, may be transformed into a composite material containing multiple sites per unit of surface area which can detect and identify multiple toxic microbial materials in a food package using the TOXIN GUARD™ system developed by Toxin Alert Incorporated and Skye Pharmatech Incorporated.

This toxin-detecting packaging can be used in conjunction with the bar-code symbol to identify the contaminated food. A double bar code system wherein one bar code identifies the food, and the other identifies the presence of a condition indicative of contamination may also be used in conjunction with the toxin-detecting packaging. As used throughout this application, "bar code" should not be limited to the linear bar codes such as those illustrated in FIGS. 13 and 14, rather, "bar codes" refers to any coded indicia that identifies the product at point of purchase, sale, or distribution. FIG. 15 illustrates one of many different types of coded indicia, other than a linear bar code, that may be used with the embodiments according to the present invention.

Bacterial metabolites as referred to in this application include the following: the production of volatile gases, pH changes from changes in the acid content, toxins, and other microbial secretions in the food. The microorganisms in the food are introduced through the diverse sources of contamination, discussed earlier, and through improper temperature management or "temperature abuse" throughout the cold chain. As used herein, temperature abuse means storage of the food product at temperatures above the optimal storage temperature, which results in bacterial or other microbial contamination of the food.

In this application, the term "volatile gases" or volatiles is used to describe gases and vapors produced by microorganisms in the contaminated food. Examples of gases produced by bacteria and other microbes in contaminated foods include carbon dioxide, hydrogen, sulfur dioxide, ammonia, organic acids, and intermediate compounds such as nitrites.

As used in this application, a "change in the pH" or an "altered pH" refers to changes in the acid content, and hence, a change in the pH unit of the food. Increased acidity is typically caused by the activity of lactic acid bacteria such as *streptococcus* and *lactobacillus* in contaminated food. Additionally, as used herein, "toxin" means chemicals, pathogenic organisms or other agents, which may be transferred from food to the consumers of the food and/or which may be toxic or result in illness in the consumer of the contaminated food products.

The invention is described in the context of bar codes because this is currently the predominant way to identify food products, including information about product type, quantity, price, unit price, and origin in a machine-readable manner. The invention is applicable, however, to other product-identifying systems, machine readable and/or readable to a human. When the term "visible" is used herein, it means visible or readable by a magnetic or electronic or other computerized bar code reader or other scanning apparatus.

Figure 2:
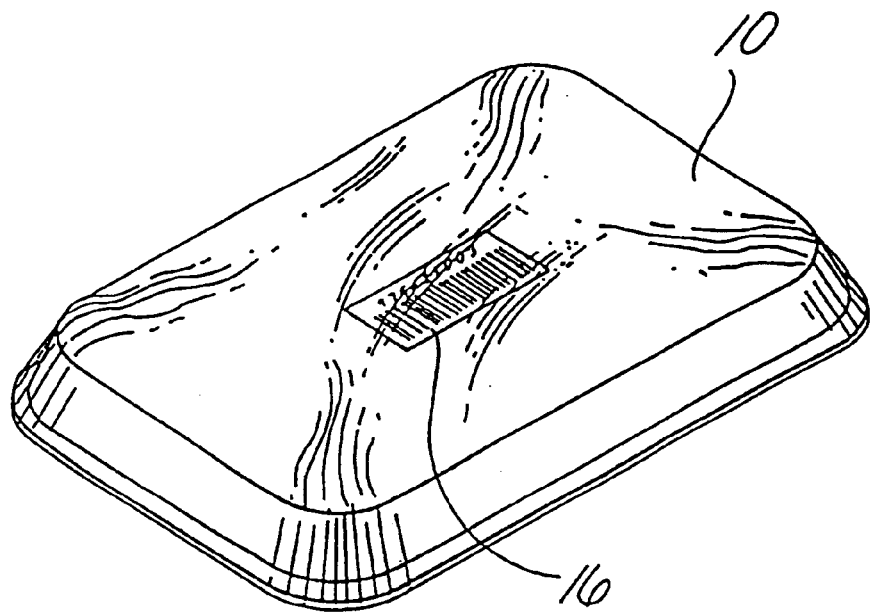
FIG. 2 is a bottom view of the packaged food product with a bar code detector system.
Figure 3:
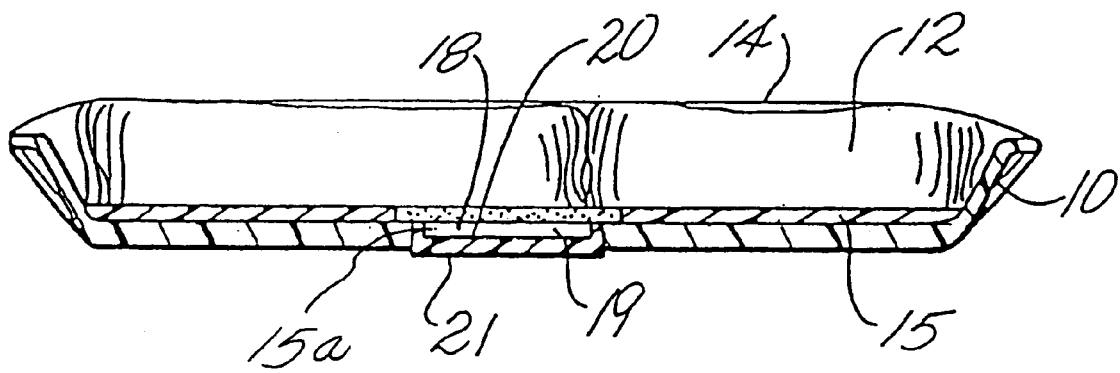
FIG. 3 is a side sectional view of the packaged food product showing the bar code detector system in the package.

Food products are often "mass produced" and sold at retail outlets, in prepackaged containers such as that illustrated in FIGS. 1–3. Typically, such packages include a STYROFOAM® (produced by The Dow Chemical Company) tray 10 which contains the food product 12; the tray and food are sealed in a transparent plastic wrap material 14 and a liner 15 lies between food product 12 and the inside bottom of the tray 10. A bar code symbol 16 is used on the products for scanning at the check-out register (FIG. 5) to reduce errors in totaling purchases and for stock control. The bar code symbol comprises a series or pattern of bars that represent a number, identifying the product. In the practice of the present invention the product-identifying system, e.g., the bar code symbol, also serves the purpose of detecting conditions indicative of contamination, including bacterial metabolites and toxins in the food products.

In the embodiment of FIGS. 1–3, a bar code symbol 16 is printed on a transparent membrane or substrate 20. One side of the substrate 20 has a self-adhesive surface for attachment to the interior of tray 10 and the other side of substrate 20 has printed on it bar code symbol 16. The bottom of STYROFOAM® tray 10 has a rectangular hole 18.

Figure 4:
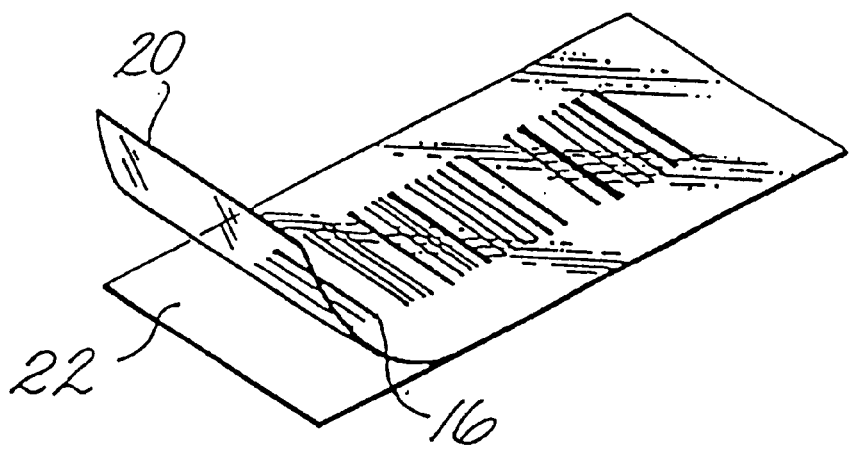
FIG. 4 is one embodiment of the bar code detector system of the present invention, prior to attachment to a food package.

Hole 18 is covered by a window 21 formed by a transparent sheet of material such as MYLAR® (a trademark of DuPont) using a suitable adhesive to seal the MYLAR® to the STYROFOAM® material around the edge of hole 18. Hole 18 and window 21 also serve as a collector 19 for liquids, juices, gases, and vapors from the food product 12 so the latter can come into contact with bar code 16. Substrate 20 can be prepared with a peelable, disposable backing or protective release layer 22 (FIG. 4), which covers bar code symbol 16 prior to its application to a package. At the site of packaging of food product 12, release layer 22 is peeled off and the adhesive side of substrate 20 is placed on the inside surface of window 21 so that bar code 16 faces the interior of the package and is exposed to the juices, or gases and vapors from the food product 12. In conventional food packaging the entire liner is generally absorbent.

In the practice of the invention, only a small portion 15 of the liner slightly larger than substrate 20 is absorbent; the remainder of the liner is preferably impervious to juices, gases, and vapors from the food, so that most of the juices, gases, and vapors from the food are channeled to substrate 20. The absorbent portion 15A of liner 15 is positioned in tray 10 in alignment with substrate 20 to maximize exposure of substrate 20 to the juices, gases, and vapors from the food. Instead of making a portion of liner 15 absorbent, a hole could be punched out of liner 15 and substrate 20 could be attached by adhesive to liner 15 around the edges of the hole. As an alternative to the described embodiment, substrate 20 could also serve as the window, in which case it would be attached to, cover, and seal hole 18 in tray 10.

In one embodiment of the invention, labeled antibodies bound to antigens form the bar code symbol. The labeled antibodies function as "ink" and are "printed" in a bar code pattern on the transparent substrate 20. First, the antigens are bound to the entire surface of substrate 20 or the portion of its surface on which the bar code symbol is to be placed. Then, a bar code printer, using the labeled antibody as the ink applies the bar code symbol to the antigen-coated surface of substrate 20.

Figure 5:
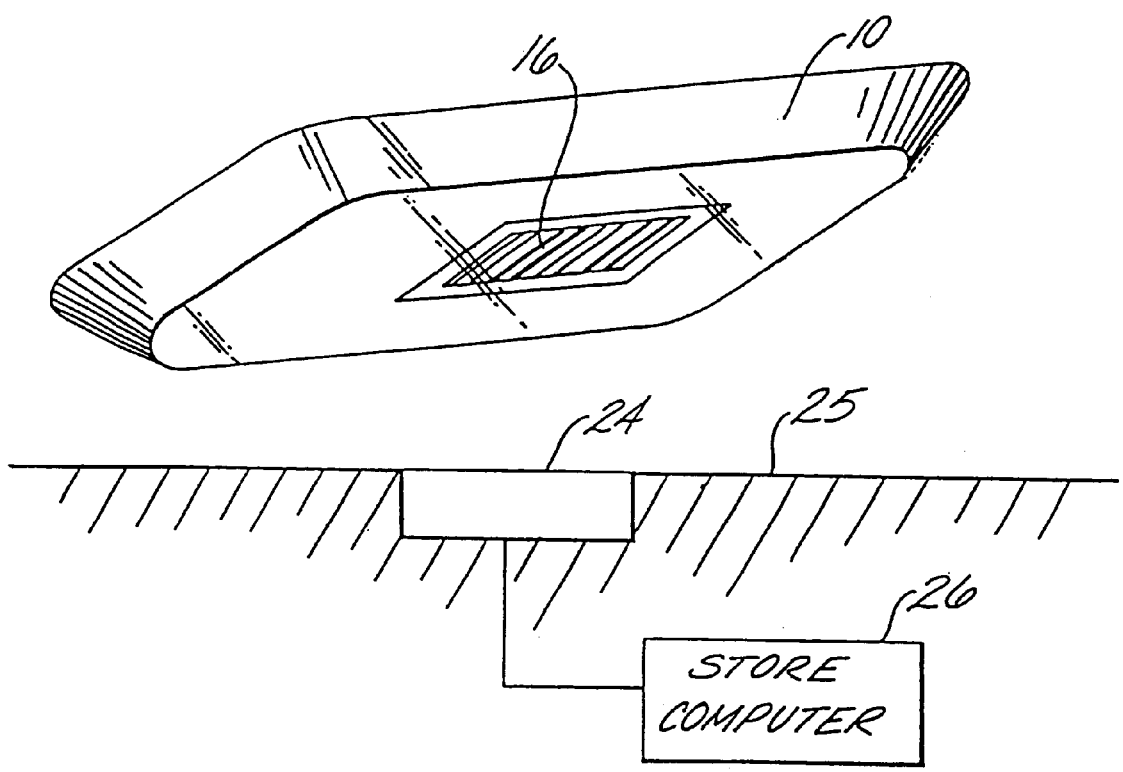
FIG. 5 is a schematic diagram of a bar code reader for use in the present invention.
Figure 6:
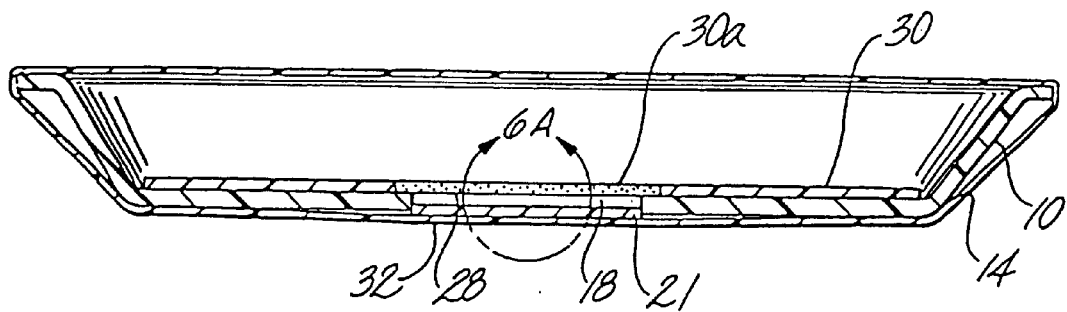
FIG. 6 is a side sectional view of another embodiment of the bar code detector system in a package tray without food.
Figure 6A:
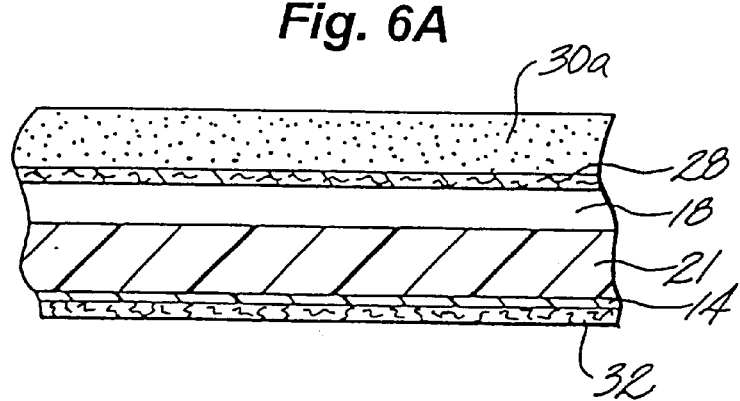
FIG. 6A is an enlarged view of part of FIG. 6.

Preferably, bar code symbol 16 serves the normal product-identifying function of a bar code, i.e., it represents price, price per unit, type of product, origin, and quantity and/or weight information. As illustrated in FIG. 5, food packages carrying the bar code detector symbol 16 are passed under a bar code scanner or reader 24 mounted on a counter 25 at the point of sale to read the product information in the usual way. A store computer 26 processes this information to calculate the amount of purchase and to manage inventory.

A bar code symbol 16 for use in the invention is prepared by irreversibly binding an antigenic determinant of bacterial metabolites, toxins or other contaminants of interest to the transparent substrate. The antigenic determinant may be a small portion of the bacterial metabolite or toxin, which is specific for that bacterial metabolite or toxin; it may be the bacterial metabolite or toxin itself, an analog of the bacterial metabolite or toxin or other compound which is capable of "mimicking" the bacterial metabolite or toxin, or pathogenic microorganisms, all of which are referred to herein as "conditions indicative of contamination."

Substrates suitable for building the bacterial metabolites and toxins are well known in the art. If substrate 20 serves as window 21 it must be impervious to the juices, gases, and vapors from the food. Suitable substrates include substrates such as those made from activated hydrophobic polyvinylidene, polyvinylidene difluoride, mixed esters of cellulose nitrate and cellulose acetate, hydrophobic laminated and unlaminated polytetrafluroethylene, microfiber glass, cellulose and polypropylene. Once bacterial metabolites and toxins are bound to the substrate, other binding sites, which remain on the substrate, are blocked by contacting them with an "inert" binding agent such as bovine serum albumin or other suitable blocking agent.

Once the bacterial metabolite or toxin is bound to the substrate, a labeled antibody, which exhibits a specificity for the bacterial metabolite or toxin, also referred to herein as anti-metabolite or anti-toxin, is bound to the bacterial metabolite or toxin. Antibodies suitable for use in the present invention include monoclonal and polyclonal antibodies. The preparation of such antibodies, specific for a desired bacterial metabolite or toxin is well known in the art. In some cases, it may be necessary to conjugate the bacterial metabolite or toxin to "mask" the toxicity of the antigen. Otherwise, injection of the toxic antigen may result in the death of the animal in which the antibodies are prepared. Methods of conjugating compounds are well known in the art and one such method is described by Hokama et al., *Mycotoxins and Phycotoxins* 188, A Collection of Invited Papers at the Seventh International IUPAC Symposium of Mycotoxins and Phycotoxins, Tokyo, Japan 1988, pp. 303–310 (Elsevier Science Publishers, Amsterdam), which is hereby incorporated by reference as if fully set forth herein.

In one embodiment of the present invention, the antibody is labeled with a colored latex bead. The preparation of antibodies labeled with colored latex beads is well known in the art. Such labeled antibodies may be prepared by diluting latex beads in a solution such as phosphate-buffered saline (8.1 mM Na2HPO4, 1.5 mM KH2PO4, 137 mM NaCl, 1.6 mM KCl) and mixing the solution gently to suspend and distribute the latex beads in the solution. Preferably, about a b 10% (wt/v) suspension of latex beads is diluted about 1:100, to give a suspension of about 0.1% (wt/v) latex beads. An antibody solution is added to the latex bead suspension. Preferably, about 0.3 to about 0.6 mg of antibodies are added for each mg of latex beads, however, this ratio will vary depending on the specificity and sensitivity of the antibody preparation and the type of support being used. The amount of antibody to be used for the preparation of labeled antibodies is derived experimentally using different dilutions of the antibody preparation. After addition of the antibody, the solution is gently mixed and incubated at about 4° C. for about 16 to about 20 hours. At the completion of the incubation, the labeled antibodies are washed with phosphate-buffered saline, and the sensitivity and specificity of the labeled antibody preparation are tested.

Coating a substrate with a pre-selected amount of bacterial metabolite or toxin tests the sensitivity and specificity of the labeled antibodies. When contacted with the labeled antibody, the labeled antibody binds to the bacterial metabolite or toxin, resulting in the development of the desired color on the substrate. Rinsing in a solution such as phosphate-buffered saline will not wash off the color that develops. Binding of the antibody to the bacterial metabolite or toxin results in the development of color for the bar code pattern forming a bar code detector system.

Figure 13:
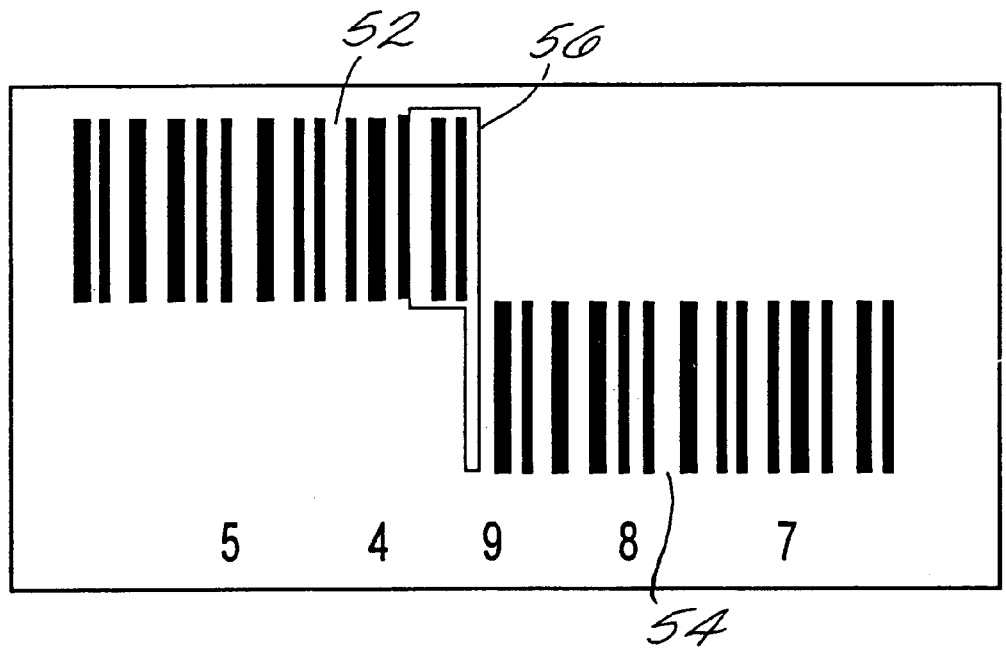
FIG. 13 shows a two bar code detector system that has not detected food contamination.
Figure 14:
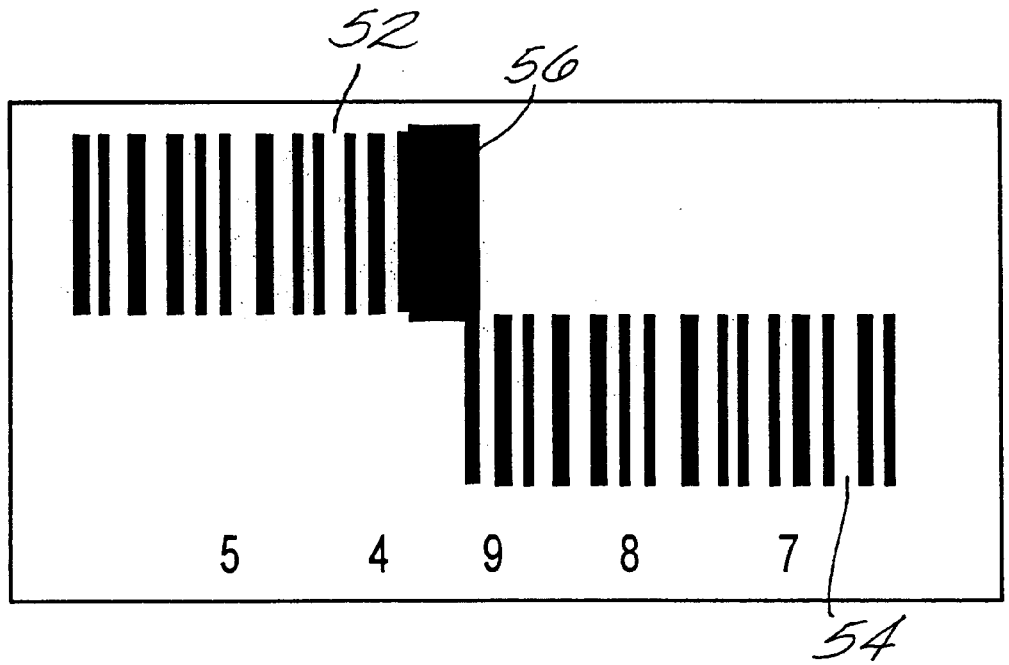
FIG. 14 illustrates a two bar code detector system that has detected food contamination.
Figure 15:
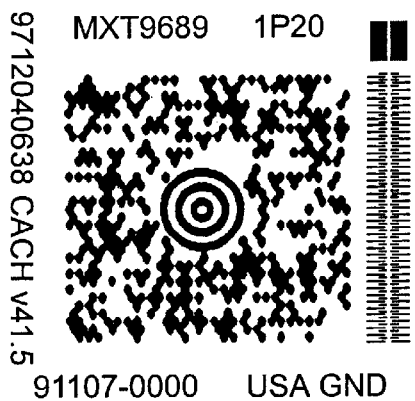
FIG. 15 shows a coded indicia other than a linear bar code that may be used with any of the embodiments of the detector system.

A preferred embodiment of such a bar code detector system is depicted in FIGS. 13 and 14. FIGS. 13 and 14 illustrate a two bar code food contamination detector system marketed under the trademark GILBAR™ by the owner of their invention. The GILBAR™ has a product identification bar code symbol 52 and a contamination detecting bar code symbol 54. Additionally the GILBAR™ has a contamination indicator area 56 which is outlined in FIG. 13 by black lines for ease in visualizing the invention; however, in practice, these lines are not present so there is no interference with a bar code scanner or reader's ability to recognize product-identification bar code symbol 52.

The GILBAR™ food contamination system alerts consumers and anyone involved at any stage in food distribution using bar code scanners or readers that a food item is contaminated as follows. In FIG. 13 the GILBAR™ has not detected contamination. In this scenario, a scanner or reader will read product-identification bar code symbol 52, but will be unable to read contamination-detecting bar code symbol 54. As shown in FIG. 14, when the food item becomes contaminated, the contamination indicator area 56 preferably changes color obliterating a portion of product-identification bar code symbol 52 and adding an additional bar to contamination-detecting bar code symbol 54. Consequently, when the food product is contaminated, a scanner or reader will be unable to read product-identification bar code symbol 52, whereas contamination-detecting bar code symbol 54 will be read. Typically, data from bar code scanners is transmitted to a computer or some centralized data collection for accounting, regulatory compliance, or other reasons. The ability to detect contaminated food products by bar code scanning creates an electronic record of whether or not a food product was contaminated from the point of sale to the consumer back through the chain of distribution.

This system is particularly advantageous to alert consumers in a grocery store or supermarket environment that typically uses fixed bar code scanners. Fixed bar code scanners are often mounted in checkout counters and are typically adapted to generate a plurality of scanning lines in three-dimensional space, which is often referred to as the "sweet spot." Supermarket or grocery store checkout clerks typically orient the bar code so it faces the scanner and then sweep the product over the scanner window. This method allows for rapid identification and pricing of products.

Occasionally, when a bar code symbol is not read the checkout clerk will type in the product identification code to allow identification and pricing of the product with the unreadable bar code. Advantageously, with the GILBAR™, when the product-identification code such as bar code symbol 52 is readable, the contamination-detecting code such as bar code symbol 54 is not readable, and vice versa. Thus, when the food item is contaminated, the product-identification bar code will not be read and the contamination-detecting bar code will be read, such that the consumer will be warned. This warning could be an alarm or a warning that would appear on the checkout register display such as the words "adulterated," "contaminated," "spoiled," or other such terms. As an alternative to this type of language, or as an addition to this type of language, the warning that would appear on the checkout register display might include the words "Do Not Sell" or the like.

The product-identification code or identification numbers may or may not be present. If they are present, the indicator area 56 of the GILBAR™ may be designed to obliterate part of the product-identification code 52 rendering it incomplete to avoid the accidental checkout of contaminated product. Additionally, the GILBAR™ indicator area 56 may include a number which appears upon contamination to complete a numeric code corresponding to the data coded by contamination-detecting bar code symbol 54. Alternatively, or in addition thereto, the colored field or indicator area 56 may be designed to obliterate the existing numeric code. With these additional elements, a checkout clerk could not inadvertently price contaminated product when bar code symbol 54 is not recognized or not read by the scanner.

Instead of bars appearing in indicator area 56, the GILBAR™ system may include bars that disappear when a toxin is present. In such an embodiment, one or more bars would disappear from product-identification bar code symbol 52 rendering the bar code unreadable while an additional bar or other element would disappear from the contamination bar code symbol 54 of indicator area 56 rendering the contamination-detecting bar code symbol 54 readable. Similarly, one or more digits of the optional pricing code could disappear from the bar code label rendering the code for product identification useless. Meanwhile, an extra number or a colored background in the indicator area 56, where the contamination numeric code is located, could disappear and thus expose the numeric contamination code.

The GILBAR™ can be used inside the package as described herein with reference to FIGS. 1–5 with bars appearing or disappearing using antibodies labeled with colored latex beads for the bar code "ink" on a substrate 20. Alternatively, the GILBAR™ can be employed with a portion of the GILBAR™ inside the package and a portion outside the package as described herein with reference to FIGS. 6–10. In the inside/outside arrangement the bar code elements found in the indicator area 56 are located on substrate 28 with the remaining elements of bar code symbols 52 and 54 aligned on the outside of the package with the interior indicator bars. In another embodiment, the indicator area 56 and the contamination-detecting bar code symbol 54 are located inside the package while the product-identification bar code is located on the outside of the package. This arrangement enhances the ability to track the source of contamination and still allows the processor, distributor, and retailer to change the product-identification bar code symbol 52.

When used with raw meat products, the contamination detector system employing the double bar code symbols or GILBAR™ may be exposed to juices, or gases and vapors from the meat. The juices, gases, and vapors from the meat may collect in the collector, and can come in contact with the antibodies and substrate associated with the double bar code detector system. Alternatively, the gases and vapors from the meat may rise up and come into contact with the labeled antibodies and the substrate associated with the coded indicia, such as double bar code symbols 52, 54, which may be located on the inside of the food package near the top portion thereof. If a bacterial metabolite or toxin is present in the juices, gases or vapors from the meat, the antibodies will release from the bar code pattern and bind to the bacterial metabolites, and/or toxins present in the juices, gases and vapors, thus, altering or destroying the coded indicia associated with the contamination detector. Antibody assays as described above are, in and of themselves, well known in the art and are referred to as competitive assays.

Accordingly, a consumer can advantageously detect the presence of the bacterial metabolite or toxin in the food product by a visual inspection of the bar code. If the consumer does not notice the alteration of the coded indicia designed to identify contaminated food, a data reader at the checkout counter (such as the one illustrated in FIG. 5) detects it, because the store computer may be configured to emit an alarm to warn that an altered indicia, such as an altered bar code symbol 52, has been detected. Further, the store computer will still be able to identify the food, quantity, price and the like by scanning the second coded indicia, such as bar code symbol 54, associated with the food contamination detector. The contaminated products can then be replaced with non-contaminated products.

A labeled antibody is one means of indicating the presence of a bacterial metabolite, toxin, or other contaminant in the juices, gases, and vapors of a food product. Those skilled in the art will be aware of other indicators, both biochemical and chemical, which are useful in the practice of the present invention. For instance, labeled DNA probes directed to microbial toxin DNA, microorganism DNA sequences, or to fragments of the microbial toxin DNA or microorganism DNA sequences may be used instead of antibodies. Furthermore, labeled RNA probes directed to microbial toxin RNA sequence, microorganism RNA sequence, or to fragments of the microbial toxin RNA or organism RNA sequences may also be utilized.

Other useful biochemical indicators include enzymatic time-temperature indicators, as described by Blixt, et al., *An Enzymatic Time/Temperature Device for Monitoring the Handling of Perishable Commodities,* Dev Biol Stand, 36:237–41 (1976), which is hereby incorporated by reference as if fully set forth herein. Chemical pH (acid-base) indicators that change color within specific pH ranges in response to dissociation of the indicator molecule on accepting or donating protons may also be useful to practice this invention. These indicators are based on the principle of microbial metabolic activity in organic systems. The most commonly used pH indicators include azo dyes, nitrophenols, phthaleins, sulfonphthaleins, aniline-sulfonphthaleins, triphenylmethane dyes, and benzaurins. Some representative pH indicators are methyl green, picric acid, cresol red, crystal violet, thymol blue, 2,4-dinitrophenol, bromophenol blue, congo red, bromocresol green, methyl red, bromophenol red, chlorophenol red, hematoxylin, and phenol red. Fluorescent indicators may be used to detect changes in the pH, partial pressure of oxygen, or the presence of metal or halide ions in the juices, gases, and vapors of the food product. In addition, chemiluminescent indicators may be used to detect various bacterial metabolites, toxins, and other contaminants in the food. Furthermore, redox indicators, such as indophenols, azines, oxazines, thiazines, indigo derivatives, and 1,10-phenanthroline complexes may be used in the practice of this invention.

Instead of destroying the coded indicia, the coded indicia could be altered in some way, e.g., by change of appearance or color, depending on the nature of the indicating system. For instance, a contaminant detector providing for the directional capillary flow of fluids from the food to where the contamination is to be detected may modify the coded indicia, making the coded indicia such as a bar code visible or invisible. Alternatively, gases and vapors may rise and come in contact with the means for changing the appearance of the indicator, causing an alteration in the data of the coded indicia, which makes the coded indicia become either visible or invisible. In general, the alteration of the coded indicia is detectable by a data reader or scanner such that contamination of products can be automatically determined by the electronics.

Thus, the embodiments of the invention present a format or vehicle to utilize existing bacterial metabolite, toxin, or other contaminant-indicating systems more effectively. The owner of this invention has marketed this format under the mark FOOD SENTINEL™, which contaminant-indicating system is disclosed in U.S. patent application Ser. No. 09/153,562, filed Sep. 15, 1998, and U.S. Provisional Application Serial No. 60/058,873, filed Sep. 15, 1997, each of which is hereby incorporated by reference as if fully set forth herein.

Figure 16:
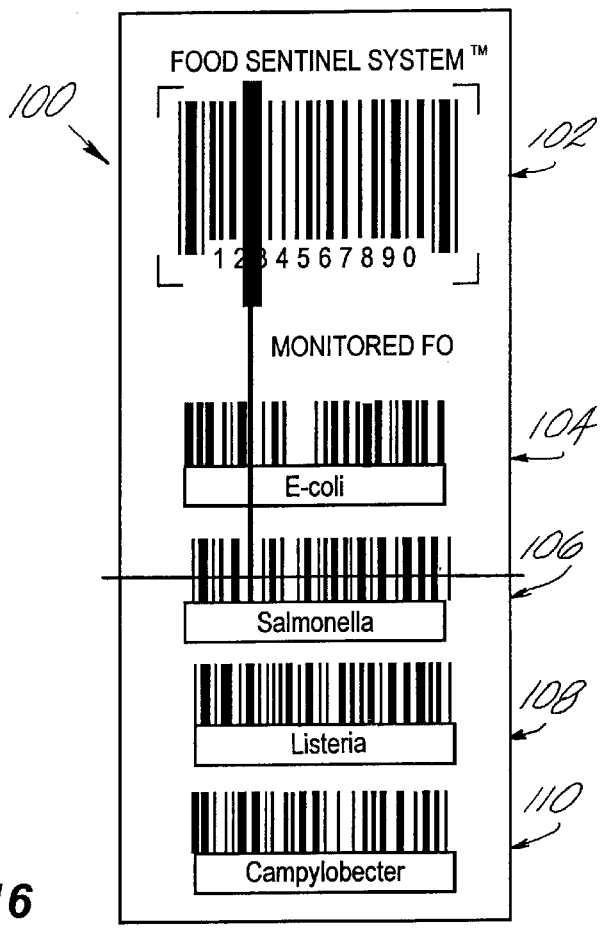
FIG. 16 illustrates an embodiment of the detector system including a first coded indicia for identifying a food product by a data reader and multiple coded indicia for respectively identifying a condition indicative of contamination in the food.
Figure 17:
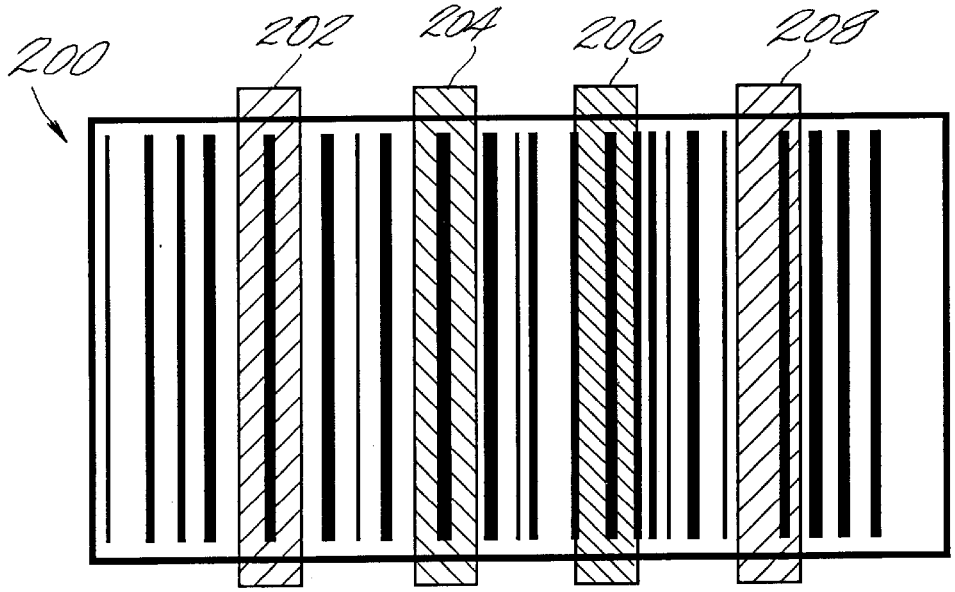
FIG. 17 illustrates a single coded indicia for identifying more than one condition indicative of contamination in food according to an embodiment of the detector system.

FIGS. 16 and 17 illustrate a contaminant-indicating system, such as that marketed under the FOOD SENTINEL™ system, wherein FIG. 16 shows a system 100 including a first coded indicia 102 for identifying a food product by a data reader. FIG. 16 also illustrates multiple coded indicia for respectively identifying a condition indicative of contamination in the food. In particular, FIG. 16 shows a second coded indicia 104, a third coded indicia 106, a fourth coded indicia 108, and a fifth coded indicia 110 each defined by an indicator bound to a substrate. Each indicator selectively identifies or indicates when a particular condition indicative of contamination in the food is present. When a particular condition indicative of contamination in the food is present, the first coded indicia 102 preferably becomes unreadable. Moreover, at least one of the second 104, third 106, fourth 108, and fifth 110 coded indicia, which codes for this particular condition, preferably becomes readable by the data reader.

FIG. 17 illustrates a single coded indicia 200 for identifying more than one condition indicative of contamination in food. Such a multi-detection bar code symbol includes an active field or contamination indicator area for each condition indicative of contamination in food sought to be identified. As shown in FIG. 17, each active field 202, 204, 206, 208 is preferably spaced apart from another; however, each active field 202, 204, 206, 208 may be arranged in an overlapping manner, a contiguous manner, or any combination thereof.

The data reader can also be used to indicate whether packaged products are in satisfactory condition at the time they left the supplier. If contaminated products are detected in the processing stream, the supplier can find out the source of contamination and implement remedial steps to ensure that the source of contamination is eliminated. For example, the same bacterial metabolite or toxin could be used for all the bars of the bar code symbol or different bacterial metabolites or toxins, including metabolites or toxins from different bacteria or other contaminants, could be used for the different bars of the bar code symbol. In this way, a number of contaminants or toxins that are commonly associated with a particular food can be detected by a single bar code symbol (such as symbol 200 illustrated in FIG. 17). Advantageously, such a symbol may be used to identify an array of different contaminating conditions, for example, during the processing stream to indicate the type of contamination and/or when the food was contaminated.

Figure 7:
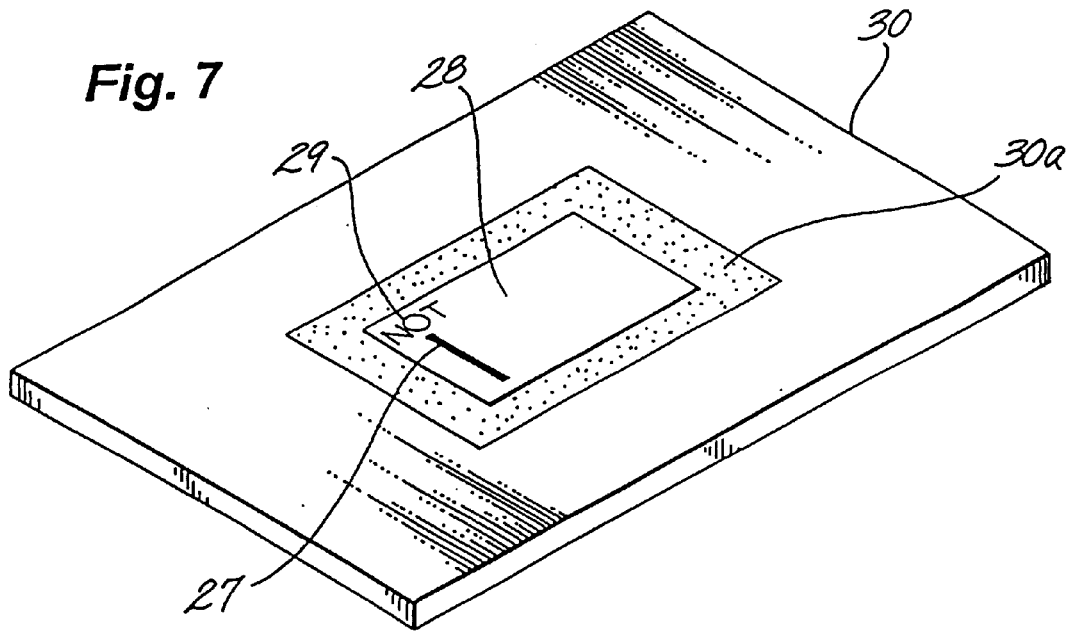
FIG. 7 is a perspective view of the bottom of the liner of FIG. 6 with one component of the bar code attached.
Figure 8:
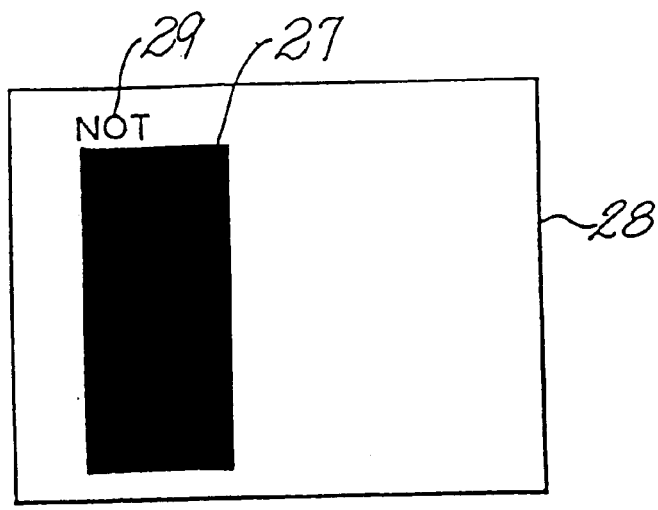
FIG. 8 is a front view of the component shown in FIG. 7.

In another embodiment of the present invention shown in FIGS. 6–10, the contamination indicator is incorporated in a bar code having two components—one component inside the package and another component outside the package. A substrate 28 is attached to the bottom of a liner 30 having an absorbent material that draws juices, other fluids, gases, and vapors away from the meat to the surface of substrate 28. Substrate 28 is preferably impervious to the juices, gases, and vapors of the food product, but it does not need to be transparent. The position of substrate 28 on liner 30 is precisely set. As illustrated in FIGS. 7 and 8, one component of the bar code comprises visible indicator elements 27 and 29 printed on the exposed surface of substrate 28. Indicator elements 27 and 29 may include a bar, a symbol, letters, or a combination thereof. In the illustrated embodiment, indicator element 27 comprises a bar, given the trademark SIRA BAR™ by the owner of this invention, and indicator element 29 comprises the work "NOT." Indicator elements 27 and 29 are printed on substrate 28 using labeled antibodies as "ink," as described above.

In this embodiment, the bottom of STYROFOAM® tray 10 has a window 21 formed by a transparent sheet of material, such as MYLAR®, using a suitable adhesive to seal the MYLAR to the STYROFOAM® material. The liner and tray are designed so the liner can be precisely positioned or "registered" in the bottom of the tray. For example, liner 30 could be dimensioned so that when it is placed in tray 10, it fills the bottom of the tray with substrate 28 in register with window 21. In this way, the close fit between liner 30 and tray 10 serves to insure that indicator elements 27 are precisely positioned with respect to the second component of the bar code, which is placed on the exterior of the bottom of tray 10 and wrap material 14. Alternatively, ridges (not shown) could be molded into the inside bottom surface of tray 10 to position liner 30 precisely and hold it in place.

Figure 9:
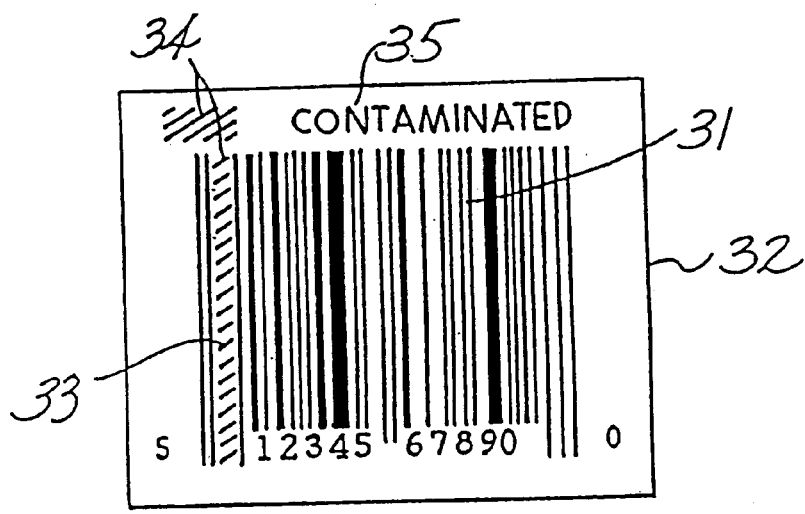
FIG. 9 is a front view of another component of the bar code detector system of FIG. 6.

As illustrated in FIG. 9, the second component of the bar code detector system preferably comprises a word 35 and a plurality of bars 31 printed on an opaque substrate 32 with ordinary ink, and cut-out sections 33 and 34 that may be cut-out with a die or "die-cut" from substrate 32. Section 33 is smaller than bar indicator element 27. Section 34 is larger than word indicator element 29. Bars 31 perform the normal product identifying function of a bar code, i.e., they represent price, unit price, type of product, origin, and weight and/or quantity. Substrate 32 has the same dimensions as window 21 and is placed on the outside of wrap material 14 so substrate 32 coincides with window 21. As a result, the position of substrate 32 is precisely set relative to substrate 28 so that indicator elements 27 and 29 are aligned or registered with cut-outs 33 and 34, respectively, and are normally visible from outside the package. Indicator element 27 completely fills cut out section 33 and indicator element 29 fits totally within cut out section 34. In the illustrated embodiment, word 35 is "CONTAMINATED."

Figure 10A:
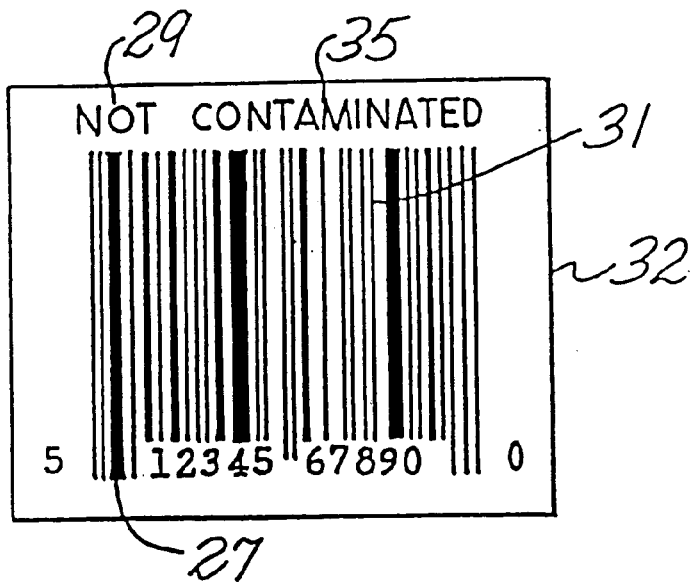
FIGS. 10A and 10B are respective front views of the components of FIGS. 8 and 9 as they appear from the outside of the food package in the presence of contamination.
Figure 10B:
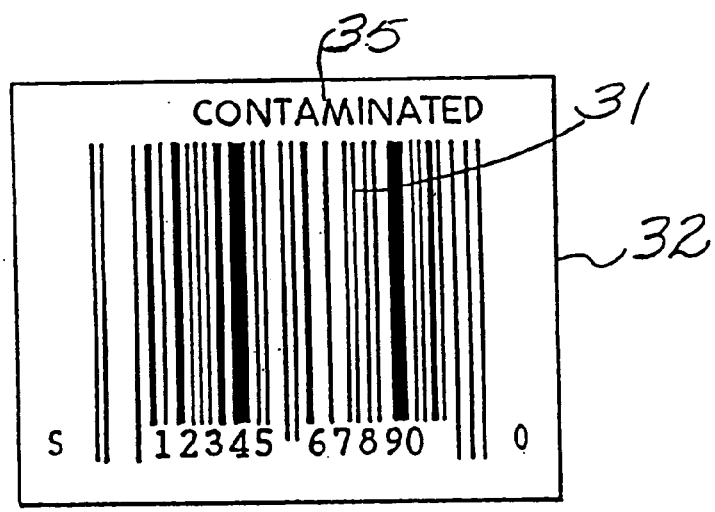

When substrates 28 and 32 are aligned, the first and second components fit together to form the bar code. As illustrated in FIG. 10A, the words "NOT CONTAMINATED" are visible from the exterior of the package and indicator element 27 and bars 31 can be read by a bar code reader when no contaminants are present in the food juices inside the package. When contaminants are present, the labeled antibodies from which indicator elements 27 and 29 are formed react with the bacterial metabolite or toxin, and are removed from the substrate 28. As illustrated in FIG. 10B, this scenario allows only word 35 and bars 31 to be visible. In the absence of element 27, the bar code reader senses that the bar code is "defective" and in the absence of element 29 humans can visually observe that the contents of the package is "CONTAMINATED."

Since it is desirable to detect different bacterial metabolites and toxins in different food products, indicator element 27 could be placed in different locations on substrate 28, depending upon the bacterial metabolite or toxin to be detected, and cut-out 33 could also be placed in different locations on substrate 32 depending upon the bacterial metabolite or toxin to be detected so it is aligned with the locations on substrate 28.

The described two component bar code detector system can be used to great advantage with the conventional bar code applicator machines used to mark food products in supermarkets. Such machines have a conveyor on which wrapped food packages are transported past a weighing station and a bar code label application station into a temporary storage bin. At the label application station, a label carrier roll is feed past a printer where the product information is printed on the bar code labels (such as substrate 32) and under a blade where the bar code labels are released from the carrier and picked up by one or more robot arms for delivery to the packages. A worker punches a product-identification code into a keypad. A controller processes the product-identification code data and the weight data and determines the product information to be printed on the label such as price, weight, unit price, and historical data or other "origin" data and controls the printer to print the bar code pattern and alphanumeric characters on the labels. The controller coordinates or times the operation so the labels are applied to the proper packages.

A preferred method will now be described for using the two component bar code with a modification of the conventional bar code applicator machines used to mark food products in supermarkets such as meat, poultry, or fish. In a central processing plant, indicator elements 27 and 29 are printed on substrates 28 with a labeled antibody or other contaminant detector as ink; then substrates 28 are respectively mounted on liners 30 in a precise relative position and packed in shipping cartons. Liners are so prepared in separate cartons for each of a number of different bacterial metabolites, toxins or contaminants and tray sizes. The cartons are shipped to the supermarkets or packaging facility where the food products are packaged in trays, wrapped, and bar code labeled with the bar code applicator machine. The packaging operation takes place in the following order:

1. For each different bacterial metabolite, toxin or contaminant, one of the corresponding liners is placed in a tray sized for the particular liner.
2. The food product is placed in the tray.
3. The food product and tray are covered with the wrap material.
4. The package is placed in a bar code applicator machine and the product-identification code is entered through the keyboard.
5. The package is weighed in the machine and transported by the conveyor to the label application station.
6. The bar code applicator machine is modified to incorporate a label-cutting die or die set in the path of the carrier between the roll and the printer. The die is adjustable in position and its position is set by the controller depending upon the particular product-identification code. Each time a bar code label passes the die, the die is actuated by the controller to form die-cut sections, such as die-cut sections 33 and 34 illustrated in FIG. 9.
7. The printer is operated by the controller to print words and bars (such as words 35 and bars 31 as shown in FIGS. 10A and 10B) on the bar code labels with ordinary ink.
8. The bar code labels are applied by the machine to a precise location on the outside of the packages in alignment with each respective substrate, such as substrate 28 illustrated in FIGS. 6–8.

In summary, the first component of the bar code, which requires tight manufacturing controls, is produced at a central processing plant. At the supermarket, workers without any special skill can reliably incorporate the first component into food product packages and add the second component of the bar code in the usual way, i.e., with a bar code applicator machine, or manually. The only special training for the workers at the supermarket is the proper selection and placement of the liner (such as liner 30 shown in FIG. 6). If a worker makes a mistake in selection or placement of a liner, bar 27 is not aligned with cutout 34 and the bar code reader senses the mistake. This technique or method provides a check to ensure that the correct bacterial metabolite or toxin-detecting bar has been used with the correct food product.

Substrate 32 is preferably opaque and white, or at least light in color to create a strong contrast with the bar codes, which are preferably printed in a dark color. For this reason cutouts 33 and 34 are required so substrate 32 does not hide visual elements 27 and 29 of substrate 28. If sufficient contrast is otherwise available, substrate 32 can be transparent and the cutouts can be eliminated.

Accordingly, to avoid the precision involved in the above-described registered embodiment, it is most preferred to form substrate 28 with a transparent sheet of material, such as MYLAR®, wherein the words and bars (such as words 35 and bars 31) are printed in ordinary black ink on a background printed in ordinary white ink. No white ink is used to define the white background where it is desired to line-up or register the respective indicator elements (such as elements 27 and 29), i.e., the areas defining the cut-out sections illustrated as sections 33 and 34 in FIG. 9 are not printed with white ink, rather, they are left transparent.

Instead of placing indicator element 27 and cutout 33 in different locations depending upon the contaminant to be detected, the location could remain fixed regardless of the type of contaminant and a visible symbol could be printed on substrate 32 near indicator element 27. For example, the letter "S" could be used for Salmonella, "E" could be used for *E. coli,* and "L" could be used for Listeria. This arrangement avoids having to incorporate an adjustable label-cutting die in the bar code applicator machine.

Figure 11:
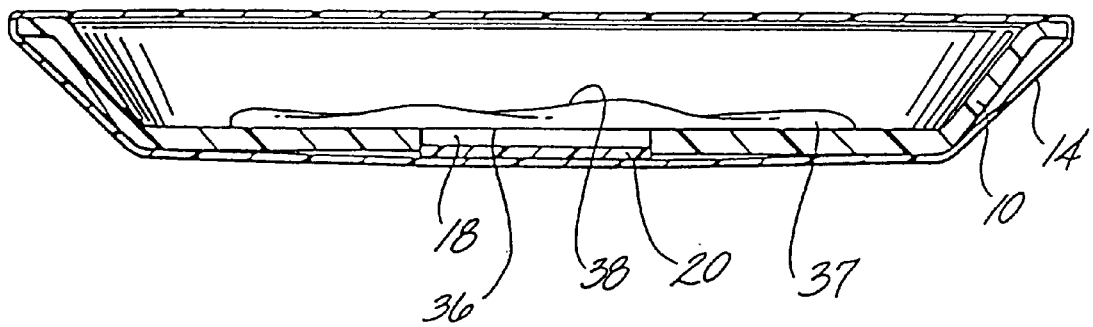
FIG. 11 is a side sectional view of another embodiment of a bar code detector system in a package tray without food.

In the embodiment of FIG. 11, the contamination indicator is also incorporated in a bar code detector system having two components—one component inside the package and another component outside the package. One component comprises a transparent bag 37 constructed from a bottom panel 36 and a top panel 38. Bag 37 is placed over hole 18 and the bottom panel 36 is secured to tray 10 by adhesive to seal hole 18 and form a window. Bottom panel 36 is fabricated from a substrate that is impervious to the juices, gases and vapors from the food. A first antibody against the toxin of interest is bound to an area of the interior surface of bottom panel 36 identical in size and shape to or larger than hole 18. Top panel 38 is fabricated from a semipermeable membrane. The top and bottom panels are sealed together at their edges by use of an adhesive or other suitable method such as heat, to form a sealed bag such as bag 37. Prior to sealing the bag, a solution including a labeled second antibody against the toxin of interest is introduced into the bag. Although the first and second antibodies could be the same, they are preferably different. Thus, the second antibody preferably recognizes different antigenic determinants on the toxin than the first antibody. The second antibody is labeled with an indicator such as a colored latex bead so that the resultant labeled antibody is of a large size. The labeled antibody, present in the solution, is at a dilute concentration so that light will readily pass through the solution and so that little or no color is discernable.

The semipermeable membrane has a pore size which is large enough to allow the toxin of interest to enter the bag, but which is small enough to prevent the labeled antibody from leaving the bag. Such membranes are well known in the art and are commercially available in a variety of pore sizes. The pore size of the semipermeable panel is selected so that the toxin of interest will pass through the semipermeable panel to the interior of the bag.

When a toxin is present in the juice, or in the gases or vapors of a meat product packed in the tray, the toxin passes into the bag through semipermeable panel 38 and binds to antibodies bound to panel 36. The toxin also binds to the labeled second antibody present in the solution in the bag. As a result, panel 36 becomes colored by the sandwich assay of the first antibody, the toxin, and the labeled second antibody, thereby indicating the presence of a toxin in the juices or the gases or vapors of the food.

The second component comprises bar code 16 printed on substrate 20, which is a transparent material such as MYLAR®. Substrate 20 is placed over hole 18 on the exterior of the food tray, and preferably outside wrap material 14. When a toxin is not present in the juices, gases or vapors from the food, panel 36 remains clear and the bar code can be easily read against the clear background. When a toxin is present in the juices, gases or vapors, the toxin binds to panel 36 and to the labeled antibody such that the substrate background becomes densely colored. In a preferred embodiment, the color of the beads used is black and the uncolored background is white or clear. The dense color of the first component prevents the bar code of the second component from being distinguished from the background by the bar code reader. This arrangement effectively obliterates or changes the bar code and indicates that the food contained in the package is contaminated.

Figure 12:
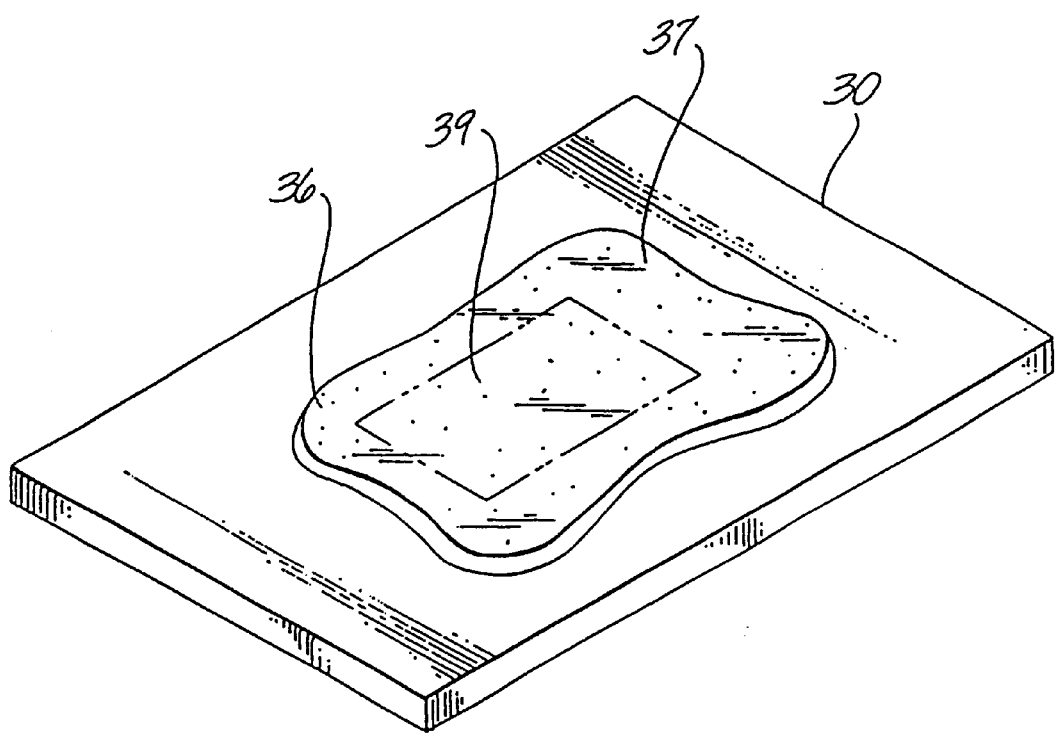
FIG. 12 is a perspective view of a liner for use in a variation of the bar code detector system of FIG. 11.

A variation of the two component bar code detector system of FIG. 11 is partially illustrated in FIG. 12. Panel 36 is secured to the underside of liner 30 using an adhesive or other suitable means of attachment. The portion 30 (not shown) of liner 30 covered by panel 36 is an absorbent material that draws juices and other fluids away from the meat to the surface of semipermeable panel 38 and serves to align bag 37 with hole 18, in the manner described in connection with FIG. 6. The remainder of liner 30 is impervious to food juices, gases and vapors. The juices pass through the semipermeable panel 38 and into the interior of bag 37. On the interior of surface of panel 36 antibodies are attached as described above. The antibodies are attached to a rectangular area 39 on the inside surface of panel 36 such that, when the liner is placed in the food tray, rectangular area 39 aligns with hole 18. Substrate 20 is attached to the outer surface of tray 10 after tray 10 has been covered with wrap material 14. A bar code is printed on substrate 20 by the bar code applicator machine. The presence of bacterial metabolites and toxins is then detected as described above.

The present invention is not to be limited to the specific embodiments shown which are merely illustrative. Various and numerous other embodiments may be devised by one skilled in the art without departing from the spirit and scope of this invention. For example, with respect to the embodiments of the present invention illustrated in FIGS. 6–12, while the invention is described for use with antibodies against a single bacterial metabolite or toxin, mixtures of antibodies against a number of different bacterial metabolites and toxins could be used. With the use of different antibodies, multiple, different bacterial metabolites and toxins that could be present in the food product can be detected. Moreover, while the invention is described primarily in relation to obliterating a bar code, the antibody bound to the substrate could also be in the form of a symbol or wording which appears, or disappears, depending on the type of antibody-toxin "assay" used. Such a symbol or wording could be read without the aid of a bar code reader. Also, while some embodiments are described in conjunction with a liner, these bar codes could also be used in the absence of a liner. Similarly, embodiments described without a liner could be used in conjunction with a liner. The scope of the invention is defined in the following claims.

What is claimed is:

1. A food contamination detector for identifying the presence of conditions indicative of contamination in food comprising:

a first bar code symbol coded to identify a food product by a bar code reader;

a second bar code symbol coded to identify contaminated food by a bar code reader;

an indicator bound to a substrate wherein the indicator is in communication with the gases and vapors from the food; and means for changing the appearance of the indicator when a condition indicative of contamination is present in the gases and vapors from the food, wherein the change in the appearance of the indicator causes the first bar code symbol to become unreadable by a bar code reader and causes the second bar code symbol to become readable by a bar code reader to identify food contamination.

2. A food contamination detector as recited in claim 1 wherein the means for changing identifies the presence of a condition indicative of contamination including bacterial metabolites and toxins.

3. A food contamination detector as recited in claim 1 wherein the indicator comprises an antibody attached to the substrate.

4. A food contamination detector as recited in claim 1 wherein the indicator comprises a time-temperature indicator associated with the substrate.

5. A food contamination detector for detecting the presence of bacterial metabolites comprising:

a tray for containing the food;

an indicator in communication with the gases and vapors from the food wherein the indicator comprises:

a first antibody attached to a substrate; and a solution in contact with the first antibody attached to the substrate, wherein the solution contains a labeled second antibody and wherein the labeled second antibody becomes bound to the substrate changing the light reflectivity of the substrate in the presence of a bacterial metabolite in the gases and vapors from the food; and a first bar code symbol coded to identify a food product aligned with the substrate so that the change in the light reflectivity of the substrate renders the first bar code symbol unreadable;

a second bar code symbol coded to identify contaminated food aligned with the substrate so that the change in the light reflectivity of the substrate renders the second bar code symbol readable to identify food contamination.

6. A food contamination detector as recited in claim 5 wherein the first antibody and the second antibody are each selected from the group consisting of monoclonal antibodies and polyclonal antibodies.

* * * * *